United States Patent
Borgmeier et al.

(10) Patent No.: US 7,225,009 B2
(45) Date of Patent: May 29, 2007

(54) APPARATUS FOR NONINVASIVELY MEASURING HEMATOCRIT AND ASSOCIATED METHODS

(75) Inventors: Paul R. Borgmeier, Salt Lake City, UT (US); Michael J. Criddle, West Valley City, UT (US)

(73) Assignee: Chi Lin Technology Co., Ltd., Hsian (TW)

( * ) Notice: Subject to any disclaimer, the term of this patent is extended or adjusted under 35 U.S.C. 154(b) by 164 days.

(21) Appl. No.: 10/694,627

(22) Filed: Oct. 27, 2003

(65) Prior Publication Data

US 2005/0090759 A1 Apr. 28, 2005

(51) Int. Cl.
*A61B 5/04* (2006.01)
*A61B 5/053* (2006.01)

(52) U.S. Cl. .................. 600/393; 600/386; 600/506
(58) Field of Classification Search ................ 600/372, 600/386, 391–393, 506, 507; 606/32
See application file for complete search history.

(56) References Cited

U.S. PATENT DOCUMENTS

| | | | | |
|---|---|---|---|---|
| 3,871,359 A | * | 3/1975 | Pacela | 600/547 |
| 4,051,842 A | * | 10/1977 | Hazel et al. | 600/391 |
| 4,353,372 A | * | 10/1982 | Ayer | 600/393 |
| 4,745,918 A | * | 5/1988 | Feucht | 606/32 |
| 4,798,208 A | * | 1/1989 | Faasse, Jr. | 600/392 |
| D326,716 S | * | 6/1992 | Mortara | D24/168 |
| 5,282,468 A | * | 2/1994 | Klepinski | 600/377 |
| 5,341,806 A | * | 8/1994 | Gadsby et al. | 600/393 |
| 2005/0070808 A1 | * | 3/2005 | Marks et al. | 600/507 |

* cited by examiner

*Primary Examiner*—Lee S. Cohen
(74) *Attorney, Agent, or Firm*—TraskBritt

(57) ABSTRACT

An interface unit for receiving a body part of a subject at which a noninvasive hematocrit measurement is to be obtained includes a narrow monitoring element with a receptacle for receiving at least a portion of the body part and contacts that are configured for establishing electrical communication with contacts of electrodes that are to be positioned over the receptacle before the body part is placed therein. In addition, the monitoring element may include a pressure port that communicates pressure into the receptacle. The interface unit also includes a cover which is configured to partially enclose the body part, to ensure that electrical communication is established between the contacts and the electrodes, and to facilitate the application of pressure to the body part. The electrodes may be in the form of electrically isolated electrode pairs, which may be formed as a strip with minimal material wastage.

21 Claims, 8 Drawing Sheets

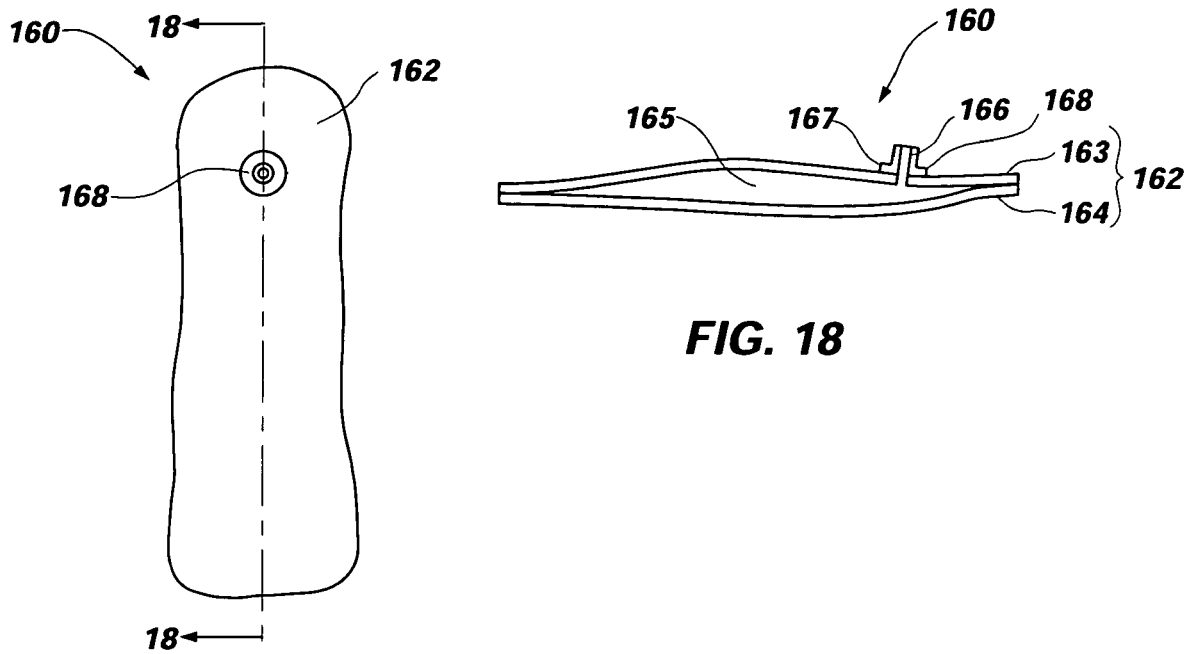
FIG. 18
FIG. 17
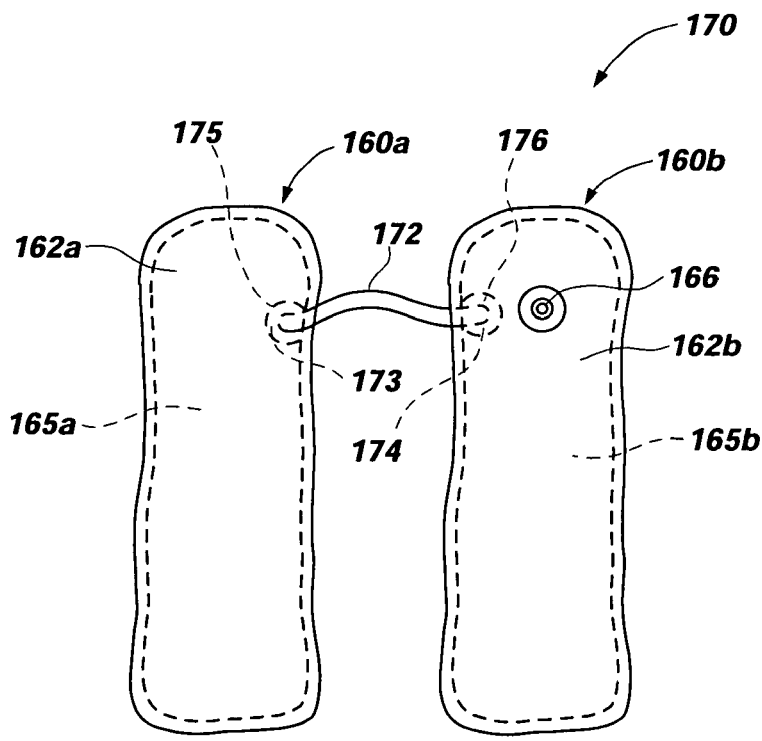
FIG. 19

APPARATUS FOR NONINVASIVELY MEASURING HEMATOCRIT AND ASSOCIATED METHODS

BACKGROUND OF THE INVENTION

FIELD OF THE INVENTION

The present invention relates generally to apparatus for use in noninvasively measuring hematocrit and, more specifically, to apparatus which are configured to effect electrical impedance and pressure plethysmography techniques to noninvasively measure hematocrit. The present invention also relates to methods for manufacturing and using the components of the hematocrit measurement apparatus.

BACKGROUND OF RELATED ART

The "hematocrit" of blood, which is defined as the percentage of whole blood volume occupied by erythrocytes (i.e., red blood cells), is an important measure of patient well-well-being in cases of trauma, blood loss by disease, iron depletion in pregnancy, dietary iron deficiency, and a number of more specific medical conditions.

Hematocrit has traditionally been measured by centrifuging a column of blood, which has been extracted from the patient, in a glass tube, until the erythrocytes are compacted by centrifugal force to one end of the tube. The hematocrit is determined by measuring the length of the tube containing dark red material and dividing by the total length of the liquid column in the tube. These length observations are usually made visually, but are also made, in some cases, by automated optical means of various designs. Besides centrifugal hematocrit determinations, hematocrit is also derived and reported by various automated blood analyzers which count erythrocytes optically in unpacked blood. This erythrocyte count correlates with packed cell hematocrit and the derived hematocrit is reported.

The above-described methods for obtaining hematocrit are invasive in that they require that blood be removed from the patient in order to determine the hematocrit. Noninvasive techniques are desirable because they are less painful, to the patient and less inconvenient, for the patient.

It has long been recognized by biomedical researchers that the electrical impedance of blood varies with hematocrit and that, as a result of this relationship, it should be possible to derive hematocrit from the measurement of blood impedance. Hematocrit has been successfully determined by measuring the impedance of blood that has been extracted from the patient and placed in an impedance measuring cell of controlled dimensions, where a fixed volume of the blood is contained, maintained at a known temperature, and agitated to maintain uniform cell distribution. Examples of such successful measurements are given by Okada and Schwan in "An Electrical Method to Determine Hematocrits," IRE Transactions in Medical Electronics, ME-7:188–192 (1960) and by deVries et al. in "Implications of the Dielectrical Behavior of Human Blood for Continuous Online Measurement of Hematocrit," Medical & Biological Engineering and Computing, pages 445–448 (1993) (hereinafter "deVries"). Like the centrifugal methods, these methods are invasive, however, and thus do not satisfy the need for a noninvasive hematocrit measurement. The impedance methods have, however, provided the inspiration for some ingenious inventions to measure hematocrit in vivo and noninvasively.

U.S. Pat. No. 5,526,808, issued to Kaminsky (hereinafter "Kaminsky"), U.S. Pat. No. 5,642,734, issued to Ruben et al. (hereinafter "Ruben"), and U.S. Pat. No. 6,128,518, issued to Billings et al. (hereinafter "Billings"), describe impedance methods for measuring hematocrit noninvasively and in vivo. These methods draw upon the observation that hematocrit determines the frequency vs. impedance profile of blood. In addition, the methods of Kaminsky, Ruben, and Billings use the pulsatile change of impedance in a finger or other limb of the body that occurs when each heartbeat pushes new blood into the organ where the measurement is made to separate the non-blood tissue impedance from the blood impedance.

The mathematical model upon which these methods are based relies upon the assumption that, as blood pulses into a finger or other body part where the hematocrit measurement is being made, the admittance (i.e., the reciprocal of impedance) change that occurs is due to the increased volume of blood providing a new current path in parallel with the old current path present before the pulse occurs. Thus, the difference in admittance between baseline, when no new blood is in the limb, and during the pulse, when new arterial blood has entered the limb, is due to the new blood. The numerical value of this admittance difference is proportional to the volume of the new blood times the admittance of the new blood.

As shown in deVries, the admittance vs. frequency characteristics of blood have a characteristic shape that depends upon hematocrit. Comparing the shapes of either the magnitude or the phase versus the frequency of the admittance, derived for the pulsed blood, against known characteristic hematocrit-dependent shapes gives a measure of hematocrit. The known characteristic shapes can be derived from a database obtained from patients having hematocrits independently measured by the centrifugal method previously described.

Additional techniques may also be used to measure the hematocrit of a patient noninvasively and in vivo. First, Ruben and Billings describe using pressure, in various ways, to change the amount of blood in the organ (e.g., the finger) at which hematocrit is noninvasively measured. Second, Ruben and Billings describe electronic systems for driving electrodes attached to the body part under measurement and for deriving phase, as well as amplitude information from impedance measurements of the body part. Third, Ruben teaches the use of a neural network computer algorithm to relate measured impedance and other data to hematocrit based upon matching a database obtained from a number of prior measurements of patients with separately-determined hematocrits.

As for apparatus that may be used to obtain such noninvasive hematocrit measurements, the teachings of Kaminsky, Ruben, and Billings are limited to four separate electrodes that must be individually wrapped around the organ at which the measurement is to be obtained and connected to the electronic system. If pressure is to be applied to the organ, a pressurization component which is separate from the electrodes is used, requiring additional assembly and potentially causing movement of the four separate electrodes from their desired positions on the organ.

Accordingly, there are needs for apparatus that improve the ease with which noninvasive hematocrit measurements may be obtained, as well as methods for manufacturing and using such apparatus.

SUMMARY OF THE INVENTION

The present invention includes apparatus that may be used in obtaining noninvasive measurements of hematocrit, or the percent, by volume, of red blood cells in the blood of an individual, noninvasively. An apparatus that incorporates teachings of the present invention includes components that are configured to effect, in combination, impedance and plethysmography techniques.

An exemplary embodiment of an apparatus according to the present invention includes an interface unit and a group of electrodes, such as electrode pairs, that may be removably secured at least partially within a receptacle of the interface unit.

Each of the electrodes is substantially planar and includes an electrical contact at an end thereof and an elongate element which is configured to contact and extend across at least a portion of a body part of a subject. Each electrode includes an electrically nonconductive backing over the entire extent thereof, a conductive layer over both the electrical contact and the elongate element thereof, and a conductive coating layer over portions of the conductive layer of the elongate element.

In a more specific embodiment, pairs of electrodes may be physically connected to one another, with the conductive layer and conductive coating layer of each electrode of the pair being discontinuous with that of the other electrode of the pair. Thus, despite the physical connection, the electrodes of the pair remain electrically isolated from one another.

At the electrical contact portion of each electrode or pair of electrodes, the conductive layer may extend across at least portions of both major surfaces, which may facilitate the ease with which a reliable electrical contact may be made to the electrode.

Each electrode may also be configured to be secured in position and, optionally, aligned relative to the receptacle of the interface unit. In this regard, each electrode may, for example, include one or more apertures that receive corresponding elements of the interface unit.

A number of electrodes may be manufactured together as a sheet, strip, or ribbon, from which individual electrodes, pairs of electrodes, or other electrode groupings may be subsequently separated. Such a sheet may, for example, be a substantially confluent member consisting essentially of two opposed series, or rows of electrode pairs.

The electrodes are configured to be assembled with the interface unit such that electrical communication is established between the electrical contact of each electrode and a corresponding contact of the interface unit. Additionally, the electrodes extend at least partially into the receptacle of the interface unit when assembled with the interface unit. Some of the contacts of the interface unit communicate with one or more corresponding power sources which, in turn, are operated under control of a processing element. Other contacts of the interface unit communicate with a monitor, which may comprise the same processing element as that which controls the power sources or a separate processing element.

In addition the interface unit includes at least one pressurization component that communicates with the receptacle. The pressurization component may communicate with a pressure source to introduce a positive pressure into the receptacle such that the positive pressure may be applied to at least a portion of a body part disposed within the receptacle. Like the one or more power sources, the pressure source may operate under control of a processing element, which may be the same as or different from that which controls the one or more power sources.

An example of the use of interface unit includes assembling four electrodes with the interface unit such that the connection between the electrical contact of each electrode and its corresponding contact of the interface unit is sufficient to facilitate electrical communication therebetween. In addition, the elongate element of each electrode is positioned so as to be located at least partially within the receptacle of the interface unit. The elongate elements of the electrodes may be arranged so that the conductive coating layers thereof will contact desired portions of a body part to be introduced into the receptacle. The body part of a subject may then be introduced into the receptacle in such a way that the conductive coating layers of the elongate elements of the electrodes are in contact therewith. Thereafter, additional contact may be established between the conductive coating layer on remaining portions of the elongate elements and the body part of the subject. Noninvasive measurement of the hematocrit of the subject, as known in the art, may then commence.

Other features and advantages of the present invention will become apparent to those of skill in the art through consideration of the ensuing description, the accompanying drawings, and the appended claims.

BRIEF DESCRIPTION OF THE DRAWINGS

In the drawings, which depict exemplary embodiments of various aspects of the present invention:

FIG. 17 is a top view of an exemplary pressurization component that may be used with the interface unit shown in FIGS. 5 and 6;

FIG. 18 is a cross-section taken along line 18—18 of FIG. 17;

FIG. 19 is a top view of an alternative embodiment of pressurization component that may be used with the interface unit of FIGS. 5 and 6;

DETAILED DESCRIPTION

Figure 1:
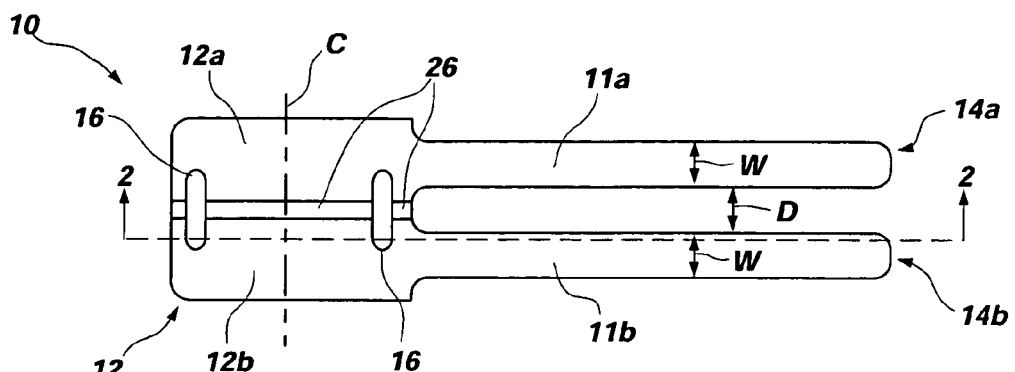
FIG. 1 is a top view of a pair of electrodes that incorporate teachings of the present invention.
Figure 2:
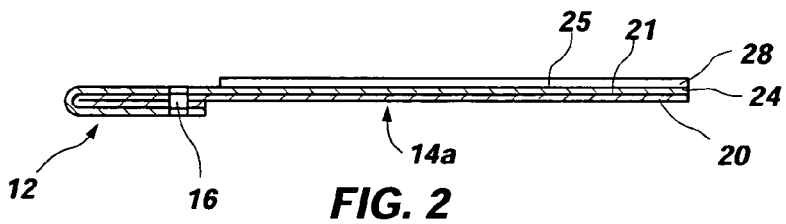
FIG. 2 is a cross-section taken along line 2—2 of FIG. 1, with a common contact region of the pair of electrodes creased along a centerline thereof.

With reference to FIGS. 1 and 2, an electrode pair 10 of the present invention is shown. Electrode pair 10 is configured for use in a system which noninvasively measures the hematocrit of a subject.

Electrode pair 10 includes a common contact region 12 and two elongate elements 14a and 14b extending therefrom. Elongate elements 14a and 14b may extend in substantially the same general direction and may be oriented parallel to one another. Each elongate element 14a, 14b includes an electrode 11a, 11b, each of which comprises a lateral extension of, and electrically communicates with a corresponding electrical contact element 12a, 12b of common contact region 12. As shown, elongate elements 14a and 14b may be substantially linear.

Structurally, electrode pair 10 may include an insulative backing 20, an electrically conductive layer 24 disposed over portions of an upper surface 21 of insulative backing 20, and, optionally, a conductive coating layer 28 positioned on portions of an upper surface 25 of electrically conductive layer 24.

Insulative backing 20 may be formed from a flexible dielectric film, such as a polymer film (e.g., polyester, such as that marketed under the trade name MYLAR® by DuPont Teijin Films of Hopewell, Va.). Conductive layer 24 may be formed from any material with suitable electrical conductivity (e.g., copper, aluminum, etc.).

Conductive coating layer 28 may be formed from an electrically conductive material, such as a conductive adhesive (e.g., a so-called "hydrogel"), a salt solution or other conductive solution, or the like.

Common contact region 12 may include at least one aperture 16 therethrough. As shown, common contact region 12 includes two apertures 16, which are positioned at approximately equal distances from a centerline C of common contact region 12, which extends transversely to a length of electrode pair 10. As will be discussed in further detail hereinafter, apertures 16 may facilitate one or more of assembly of electrode pair 10 with an interface unit 50 (FIG. 21), alignment of electrode pair 10 relative to a receptacle 92 of a monitoring element 90 of interface unit 50, and alignment of electrical contact elements 12a, 12b with corresponding contacts 107 (FIG. 20) of interface unit 50.

Electrical contact elements 12a and 12b form a common contact region 12 of electrode pair 10. Electrical contact elements 12a and 12b, which are formed by separate portions of electrically conductive layer 24, are electrically isolated from each other by a discontinuity 26 in electrically conductive layer 24 that extends completely across common contact region 12, but are physically connected to one another by the portion of insulative backing 20 located within common contact region 12.

Elongate elements 14a and 14b individually extend from common contact region 12, with electrodes 11a and 11b extending from their respective electrical contact elements 12a and 12b. Thus, electrodes 11a and 11b are physically separate from one another. The electrically conductive layer 24 and conductive coating layer 28 of each elongate element 14a, 14b are discrete and electrically isolated from the corresponding layers of the other elongate element 14b, 14a, rendering elongate elements 14a and 14b electrically discrete from one another. The combination of the separation between elongate elements 14a and 14b and the presence of discontinuity 26 between electrical contact elements 12a and 12b electrically isolates electrode 11a and electrode 11b from one another.

Further, the distance D by which elongate elements 14a and 14b are separated may be substantially the same as the width W of an elongate element 14a, 14b. Such a configuration facilitates the formation of electrode pairs 10 from a strip 40, depicted in FIG. 3, that comprises a laminate of insulative backing 20, conductive layer 24 covering portions of insulative backing 20 over which conductive structures are to be formed, and conductive coating layer 28, which extends substantially centrally along the length of strip 40, at a location from which elongate elements 14a and 14b of electrode pairs 10 will be formed.

As shown, strip 40 may include two opposed, offset rows 42 and 44 of electrode pairs 10A, 10B, 10C, etc., and 10A', 10B', 10C', etc., each of which comprises an electrode pair 10 (FIGS. 1 and 2). Common contact regions 12 of electrode pairs 10 may be positioned and aligned along opposite long edges 41 and 43 of strip 40, with common contact regions 12 of adjacent electrode pairs 10 of the same row 42, 44 being positioned adjacent to one another. Electrical isolation between adjacent electrical contact elements 12a and 12b of adjacent electrode pairs 10 occurs as the adjacent electrode pairs 10 are physically separated from one another.

Elongate elements 14a and 14b of electrode pairs 10A, 10B, 10C, etc., and 10A', 100B', 10C', etc., of both rows 42 and 44, respectively, are formed centrally along the length of strip 40. Elongate elements 14a and 14b of electrode pairs 10A, 100B, 10C, etc., of one row 42 mesh, or are interleaved with, elongate elements 14b and 14a of electrode pairs 10A', 100B', 100C', etc., that are located in the other row 44. Thus, an elongate element 14a of each electrode pair 10A', 10B', 100C', etc., 10A, 10B, 100C, etc., of row 44, 42 is located between elongate elements 14a and 14b of each electrode pair 10A, 10B, 10C, etc., 10A', 10B', 10C', etc., of row 42, 44. In addition, elongate elements 14b and 14a of adjacent electrode pairs 10A, 10B, 10C, etc., 10A', 10B', 10C', etc., in the same row 42, 44 are separated are from one another by elongate elements 14b and 14a of electrode pairs 10A', 10B', 10C', etc., 10A, 10B, 10C, etc., of the other row 44, 42.

Figure 3:
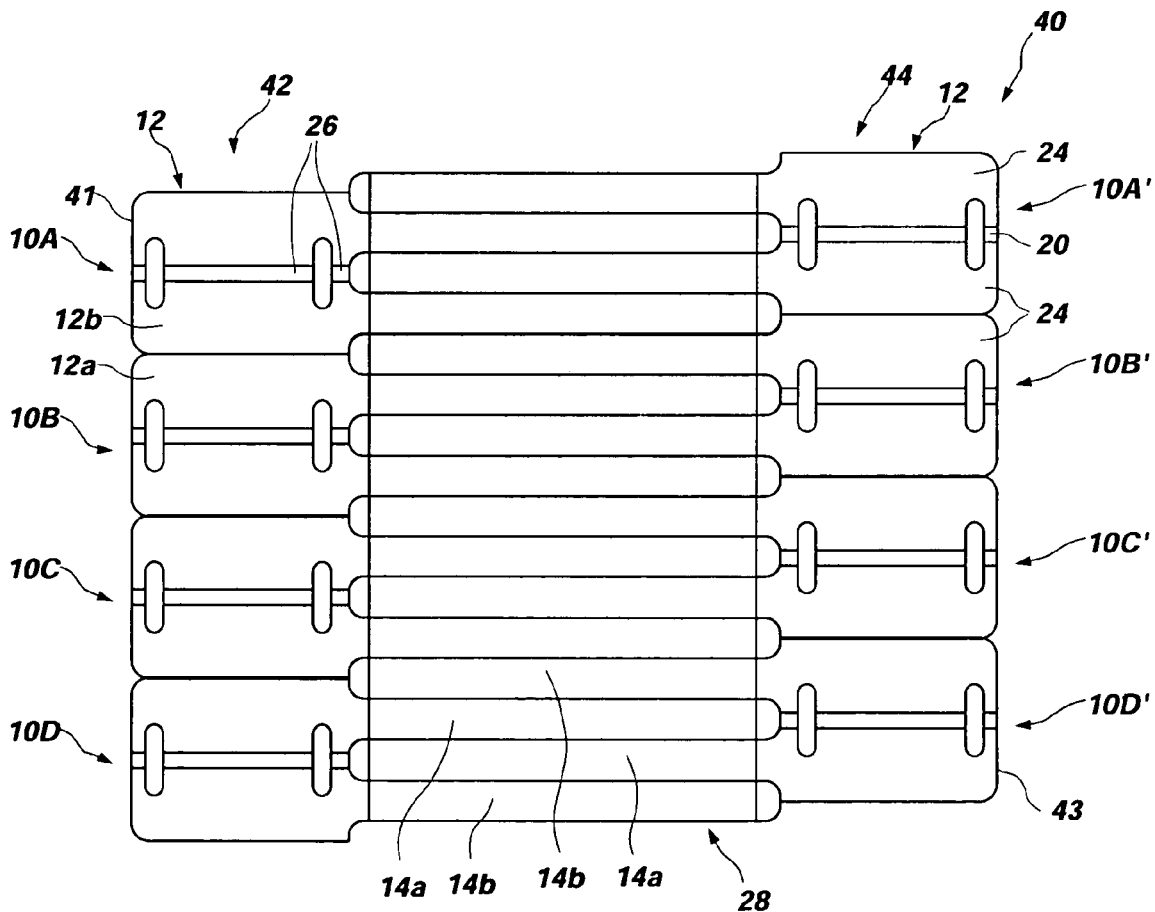
FIG. 3 is a top view of a strip including a plurality of electrode pairs of the type shown in FIG. 1.
Figure 4:
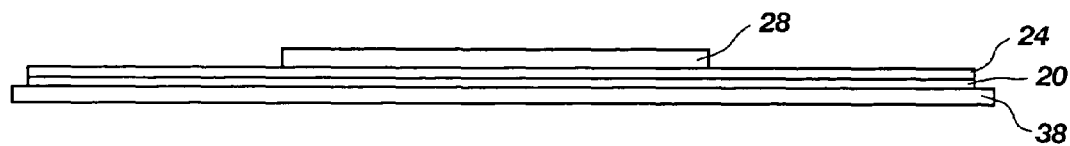
FIG. 4 is a cross-sectional representation of the strip shown in FIG. 3.

As an example of a process for manufacturing strip 40, an insulative film (i.e., insulative backing 20), a conductive film (i.e., conductive layer 24), and a conductive coating (i.e., conductive coating layer 28) may be laminated to one another by known processes. Optionally, as depicted in FIG. 4, strip 40 may include a support layer 38 upon which the other layers of the laminate are carried and from which the remainder of the laminate may be peeled and which may be formed from any suitable material known in the art (e.g., a plastic-coated or wax-coated paper). Portions of conductive layer 24 may be removed, either before or after lamination is effected, to form discontinuities 26 (FIGS. 1 and 3). Following lamination, electrode pairs 10 and the various features thereof (including apertures 16) are formed and, thus, at least partially separated from one another.

By way of nonlimiting example, known die cutting processes may be used to form electrode pairs 10. Optionally, electrode pairs 10 and discontinuities 26 within conductive layer 24 thereof may be formed simultaneously, such as with a die that includes cutting edges of different heights (i.e., a taller edge to define electrode pairs 10 and apertures 16 and a shorter edge to cut material out of conductive layer 24 to form discontinuities 26). If strip 40 includes a support layer 38, electrode pairs 10 may be defined without cutting completely through support layer 38, which maintains the relationship of electrode pairs 10 until use thereof is desired.

By forming electrode pairs 10 in this way, material wastage is minimized, electrode pairs 10 are easier to store, and the likelihood that electrode pairs 10 will be damaged prior to use is minimized.

Figure 5:
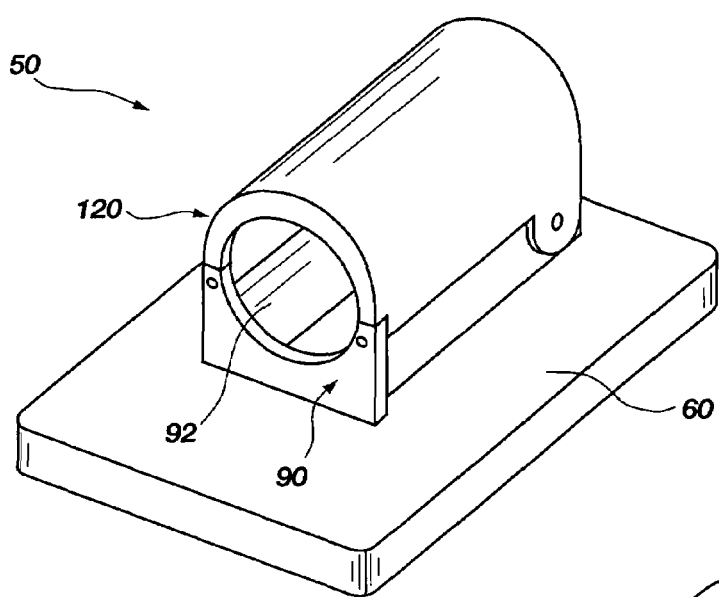
FIG. 5 is a perspective view of an exemplary interface unit of the present invention, showing a cover of the interface unit in a closed orientation over a monitoring element thereof.
Figure 6:
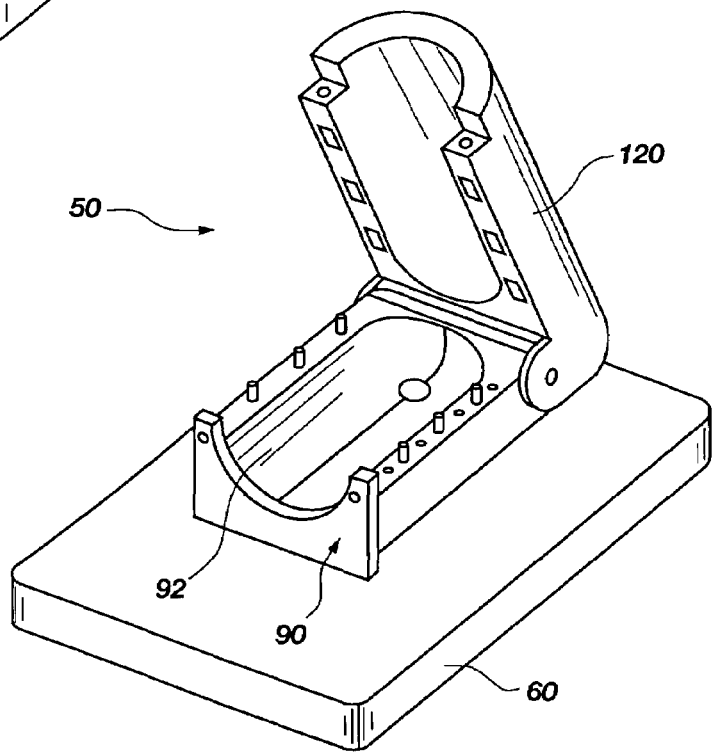
FIG. 6 is a perspective view of the interface unit of the present invention, with the cover in an open orientation relative to the monitoring element.

Turning now to FIGS. 5 and 6, an exemplary embodiment of an interface unit 50 of the present invention is depicted. Interface unit 50 includes a monitoring element 90 that includes a receptacle 92 which is configured to at least partially receive a body part of a subject and a cover 120 which is configured to be coupled with monitoring element 90 in such a way as to at least partially enclose the body part within receptacle 92. In the exemplary embodiment shown in FIGS. 5 and 6, cover 120 is configured to be hingedly coupled with and uncoupled from monitoring element 90. Interface unit 50 may also include a base 60, which supports monitoring element 90 and cover 120.

Figure 7:
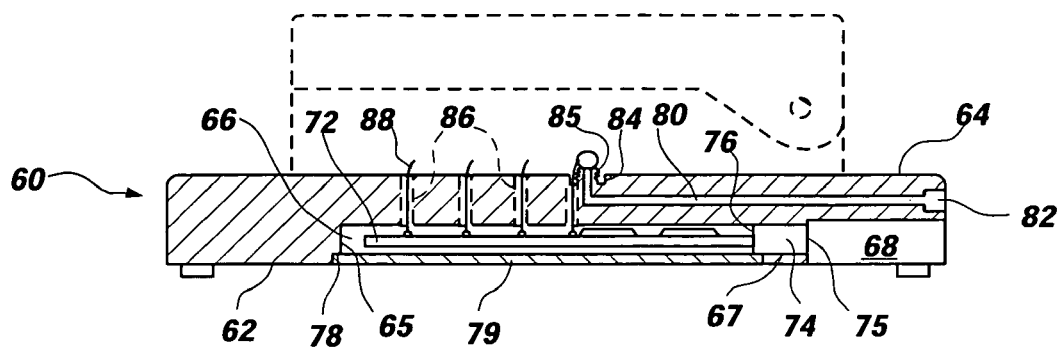
FIG. 7 is a cross-sectional representation of a base of the interface unit shown in FIGS. 5 and 6.
Figure 8:
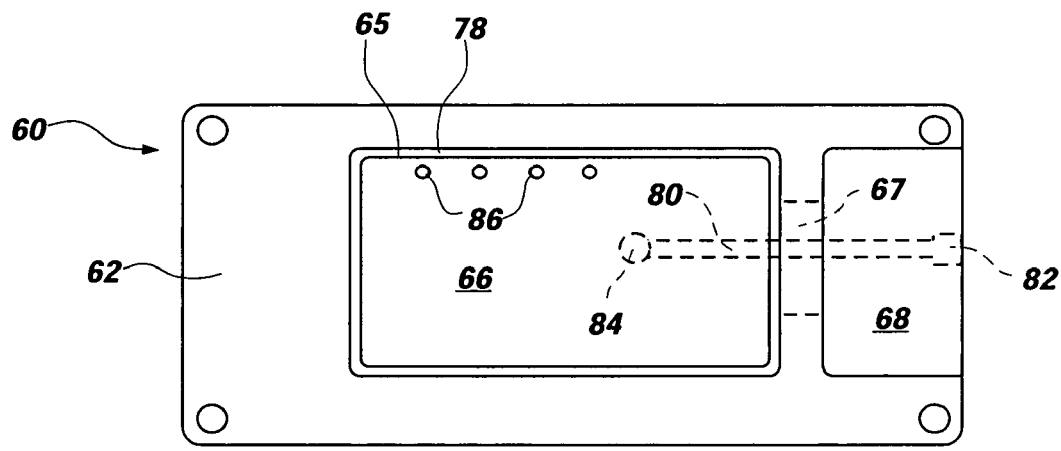
FIG. 8 is a bottom view of the base of FIG. 7.
Figure 9:
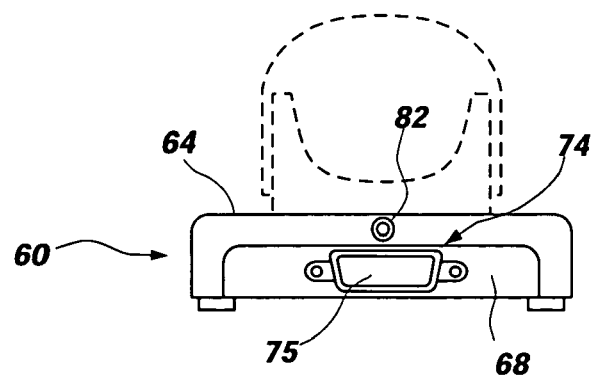
FIG. 9 is a rear view of the base shown in FIGS. 7 and 8.

A specific example of a base 60 of an interface unit 50 that incorporates teachings of the present invention is pictured in FIGS. 7 through 9.

Base 60 may be configured to house various components of interface unit 50 (FIGS. 5 and 6). In this regard, base 60 may include an interior componentry receptacle 66, as well as a connection receptacle 68 which is continuous with an exterior of base 60, apertures 67 for facilitating communication between connection receptacle 68 and componentry receptacle 66, and a conduit 80 for directing the flow of air or other gases to desired locations.

FIGS. 7 and 8 illustrate base 60 as including a componentry receptacle 66 which includes an opening 65 that is continuous with bottom surface 62 of base 60. Componentry receptacle 66 may be configured to receive electronic components of interface unit 50 (FIGS. 5 and 6), such as the depicted circuit board 72 (with one or more semiconductor devices and other electronic devices thereon) computer cables, or other electrical wires.

Each communication port 74, which is configured to establish communication between the semiconductor device(s) on circuit board 72 and one or more electronic devices (e.g., a computer, a display, a printer, etc.) (not shown in FIGS. 7 through 9) that are external to interface unit 50 (FIGS. 5 and 6), may be disposed within an aperture 67 located between componentry receptacle 66 and connection receptacle 68. A coupling end 75 of communication port 74 is exposed to connection receptacle 68 and, thus, to the exterior of base 60, while an interior end 76 of communication port 74 is operatively coupled to circuit board 72 or to a computer cable.

Communication port 74 may comprise any known type of communication port, such as a multi-pin connection port, a USB port, a wireless port of a known type (e.g., infrared (IR), radiofrequency (RF), etc.), or the like. Communication port 74 provides an interface by which the electronic components that are carried by circuit board 72 may communicate with one or more output elements (e.g., monitors, printers, etc.) or processing elements (e.g., computer processors, computers, etc.) (not shown).

Componentry receptacle 66 may be enclosed by an access panel 79, which is configured to cover opening 65 and, optionally, facilitate access to componentry receptacle 66 and the elements disposed therein. In order to position access panel 79 flush with bottom surface 62 of base 60, an inset ledge 78 may be formed in bottom surface 62 around at least a portion of opening 65 of componentry receptacle 66. Inset ledge 78 is configured to receive access panel 79 without permitting access panel 79 to be inserted into componentry receptacle 66, as well as to facilitate securing of access panel 79 to base 60. Access panel 79 may be secured to base 60 by any suitable technique. For example, bolts may be used to secure access panel 79 in place over opening 65, or it may be secured in place by way of one or more latches, a combination of hinges and latches, by way of a sliding mechanism, or otherwise.

A conduit 80 facilitates the communication of positive pressure from an external pressure source (not shown in FIGS. 7 through 9) to pressurization components 160 (FIGS. 17 through 19) that have been assembled with interface unit 50 (FIGS. 5 and 6), which will be described in further detail hereinafter. As shown, conduit 80 extends through base 60 between a desired location at an exterior surface thereof, such as an edge located adjacent to connection receptacle 68, and a desired location on an upper surface 64 thereof. Both a first end 82 of conduit 80 that opens to connection receptacle 68 and an opposite, second end 84 of conduit 80 that communicates with upper surface 64 are configured so as to facilitate the coupling of hose barbs 85 or other pressure ports of known type thereto. By way of example only, ends 82 and 84 may be threaded so as to engage complementary threading on the exterior of hose barbs 85.

Base 60 may also include conduits 86 which extend between componentry receptacle 66 and upper surface 64. In the illustrated example, base 60 includes four conduits 86. Conduits 86 are configured to receive electrical wires 88 which extend between circuit board 72 and corresponding electrical contacts 107 (FIG. 11) of monitoring element 90 of interface unit 50 (FIGS. 5 and 6).

Figure 10:
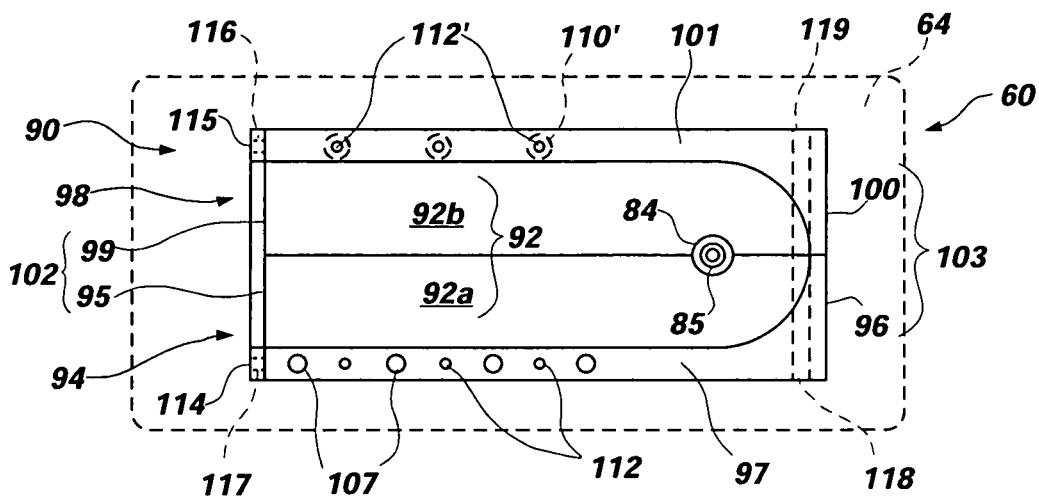
FIG. 10 is a top view of the monitoring element of the interface unit depicted in FIGS. 5 and 6.
Figure 11:
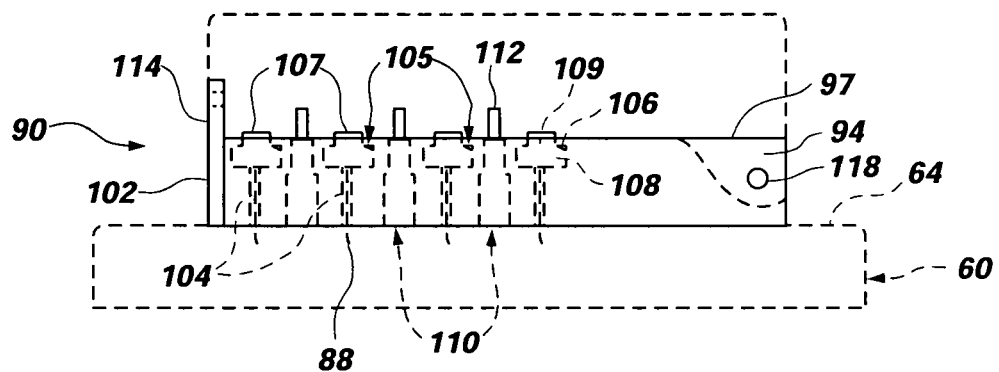
FIG. 11 is a side view of the monitoring element of FIG. 10.
Figure 12:
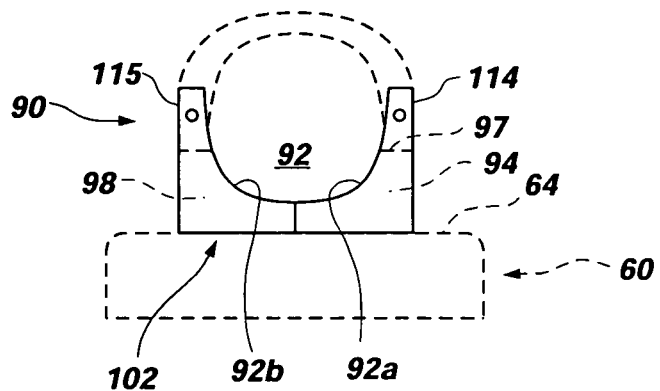
FIG. 12 is a front view of the monitoring element illustrated in FIGS. 10 and 11.

Turning now to FIGS. 10 through 12, an example of a monitoring element 90 of an interface unit 50 (FIGS. 5 and 6) that incorporates teachings of the present invention is illustrated.

Monitoring element 90 is disposed on upper surface 64 of base 60. Monitoring element 90 includes two sides 94 and 98, which protrude generally upwardly from upper surface 64 of base 60. Each side 94, 98 forms a half 92a, 92b of receptacle 92. Second end 84 of conduit 80 (FIGS. 7 and 8) is exposed to receptacle 92, for example, between sides 94 and 98, and may include a hose barb 85 of a known type disposed therein. Halves 92a and 92b of receptacle 92 are configured to, in combination, receive at least a portion of a body part of a subject, such as a human finger. Each side 94, 98 also includes an upper edge 97, 101, respectively. Corresponding ends 95, 99 and 96, 100 of sides 94 and 98 respectively form a front 102 and a rear 103 of monitoring element 90.

Conduits 104, which are configured to communicate with corresponding conduits 86 in base 60 (FIGS. 7 and 8), extend through the height of side 94, opening to contact receptacles 105 formed in upper edge 97. The number of conduits 104 and contact receptacles 105 within side 94 corresponds to the number of conduits 86 in base 60. As shown, there may be four conduits 104 and four contact receptacles 105 in side 94.

Each contact receptacle 105 is configured to receive and retain a corresponding contact 107, which, in turn, is coupled to a corresponding electrical wire 88. Each contact 107 may be retained within its corresponding contact receptable 105 with an adhesive material or mechanically (e.g., by way of the depicted retaining ledge 106, which covers a circumferential ledge 108 and laterally surrounds a protruding element 109 of contact 107), as known in the art.

In addition, guide pin receptacles 110 are formed within upper edge 97 of side 94. Each guide pin receptacle 110 may be positioned between an adjacent pair of contact receptacles 105.

Guide pin receptacles 110 are configured to receive and retain guide pins 112. Guide pin receptacles 110 may be configured to rigidly secure guide pins 112 at the desired position. By way of example only, guide pin receptacles 110 may comprise substantially cylindrical receptacles within which guide pins 112 may be adhesively secured, or threaded receptacles into which guide pins 112 may be screwed.

Guide pins 112 may be unitary members which are configured to remain in a fixed position. Alternatively, guide pins 112 may comprise spring-loaded pistons that may be compressed, then resiliently return to an extended position.

Side 98 may likewise include guide pin receptacles 110' formed in upper edge 101 thereof and guide pins 112' protruding from upper edge 101. Guide pin receptacles 110' and guide pins 112', which may be aligned across receptacle 92 from corresponding guide pin receptacles 110 and guide pins 112, are useful for maintaining electrode pairs 10 (FIG. 21) that are adjacently positioned across receptacle 92 in electrically isolated relation to one another.

Monitoring element 90 may be configured such that cover 120 (FIGS. 13 through 15), when oriented appropriately over monitoring element 90, may be secured or locked in position relative thereto. As shown in FIGS. 10 through 12, in one example of such a configuration, front 102 of monitoring element 90 may include a pair of protruding elements 114 and 115 corresponding to sides 94 and 98, respectively, of monitoring element 90. Protruding elements 114 and 115 may protrude in a direction which is substantially perpendicular to the plane or planes in which upper edges 97 and 101 are located. Protruding elements 114 and 115 may be configured to be positioned adjacent to a front 132 of a cover 120 (FIGS. 13 and 14) and to facilitate securing of cover 120 in a closed position over monitoring element 90. In this regard, each protruding element 114, 115 may include an aperture 116, 117 or other feature which is configured to engage or to be engaged by a corresponding feature of a locking element 140 (FIG. 16) to be used with cover 120.

Figure 13:
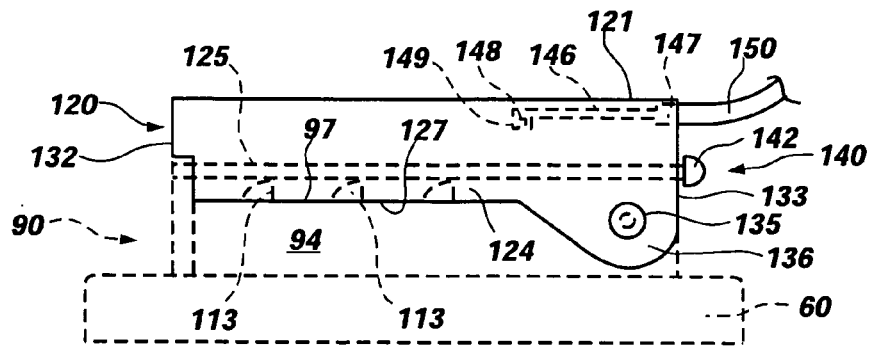
FIG. 13 is a side view of a cover of the interface unit pictured in FIGS. 5 and 6.
Figure 14:
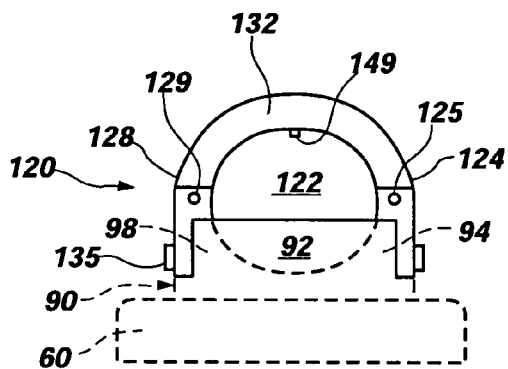
FIG. 14 is a front view of the cover of FIG. 13.
Figure 15:
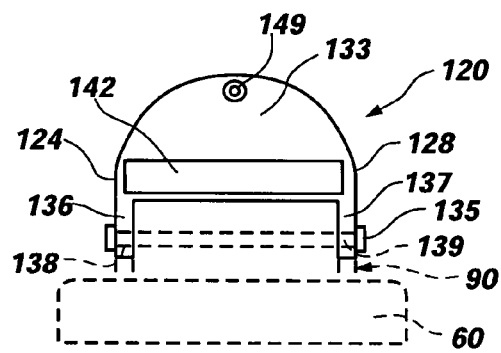
FIG. 15 is a rear view of the cover shown in FIGS. 13 and 14.
Figure 16:
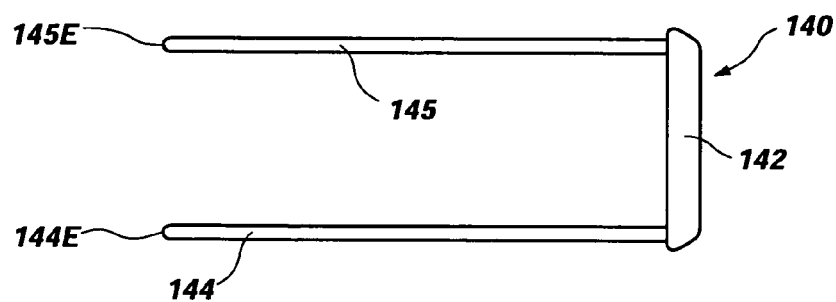
FIG. 16 is a top view of a locking element that may be used with the cover of FIGS. 13 through 15 and the monitoring element shown in FIGS. 10 through 12.

Monitoring element 90 may be permanently coupled to cover 120 (FIGS. 13 through 15). By way of example only, monitoring element 90 may be configured for hinged attachment to corresponding features of cover 120. In this regard, sides 94 and 98 of monitoring element 90 may include aligned apertures 118 and 119, respectively, formed longitudinally (relative to the orientation of base 60) therethrough to receive one or more hinge pins 135 (FIG. 13).

Referring now to FIGS. 13 through 15, an exemplary cover 120 of an interface unit 50 (FIGS. 5 and 6) according to the present invention is shown. As illustrated, cover 120 is configured to be positioned over at least a portion of monitoring element 90. When cover 120 is positioned, as intended, over monitoring element 90, two opposite sides 124 and 128 thereof are positioned over corresponding sides 94 and 98, respectively, of monitoring element 90.

Cover 120 also includes a receptacle 122 which communicates with receptacle 92 of monitoring element 90. Like receptacle 92, receptacle 122 is configured to receive at least a portion of a body part. When the body part is disposed within receptacle 92 and cover 120 is appropriately positioned over monitoring element 90, receptacle 122 also receives a portion of the body part.

Cover 120 may be secured in position relative to one or both of monitoring element 90 and base 60. In the example of cover 120 shown in FIGS. 13 through 15, two connection elements 136 and 137 protrude downwardly from sides 124 and 128, respectively, at or near a rear 133 of cover 120. Connection elements 136 and 137 are located in planes which are substantially parallel to a length of cover 120. Each connection element 136, 137 includes an aperture 138, 139, respectively, which is configured to align with a corresponding aperture 116, 117 (FIG. 10) of a side 94, 98 of monitoring element 90 and, thus, to mutually receive a hinge pin 135 that has also been disposed through its corresponding aperture 116, 117.

When cover 120 is positioned over monitoring element 90 with receptacles 92 and 122 in communication, a biasing surface 127 at or adjacent to a lower edge of side 124 of cover 120 and adjacent to an edge of receptacle 122 is positioned over upper edge 97 of side 94 of monitoring element 90. Biasing surface 127 may be biased against either upper edge 97 or electrical contacts 12a, 12b (FIG. 21) of each electrode pair 10 that has been positioned on or over upper edge 97. In order to prevent electrical shorting between electrical contacts 12a and 12b, biasing surface 127 may be formed from or coated with a dielectric material.

If guide pins 112, 112' (FIGS. 10 and 11) that protrude from upper edge 97 are in fixed positions, pin receptacles 113 may be formed in biasing surface 127, as well as in the bottom edge (not shown) of side 128. Due to the hinged arrangement of cover 120 and monitoring element 90 in the depicted example, pin receptacles 113 are somewhat arced so as to facilitate their receipt of fixed guide pins 112.

Cover 120 may also be configured to be secured or locked into a desired orientation over monitoring element 90. As a nonlimiting example, cover 120 may include a locking element 140 of the type depicted in FIG. 16. Locking element 140 may include an actuator handle 142 which is configured to be positioned adjacent to rear 133 of cover 120. Locking element 140 also includes two substantially parallel locking arms 144 and 145 that protrude from actuator handle 142. Locking arms 144 and 145 may be disposed within conduits 125 and 129, respectively, which extend through the lengths of sides 124 and 128 of cover 120 and which align with apertures 116 and 117 (FIGS. 10 through 12) of monitoring element 90.

As shown in FIGS. 13 through 16 when cover 120 is in a closed position over monitoring element 90, actuator handle 142 of locking element 140 may be biased toward rear 133 of cover 120 and rear 103 of monitoring element 90. As actuator handle 142 is moved in this fashion, locking arms 144 and 145 slide through their respective conduits 125 and 129 and the ends 144E, 145E of locking arms 144 and 145 are introduced into apertures 116 and 117 of monitoring element 90, thereby locking cover 120 into a closed position over monitoring element 90. When opening of cover 120 is desired, actuator handle 142 of locking element 140 may be pulled away from rear 133 of cover, thereby moving locking arms 144 and 145 in the reverse direction through conduits 125 and 129 and out of apertures 116 and 117 of monitoring element 90.

Cover 120 may also be configured to facilitate the application of a positive pressure to a portion of a body part disposed within receptacle 122 thereof. For example, but not to limit the scope of the present invention, cover 120 may include a conduit 146 that extends from an exterior surface 121 thereof to receptacle 122. An end 147 of conduit 146 that opens to exterior surface 121 of cover 120 may be configured to facilitate disposal of a tube 150 or other conduit in communication therewith. The other end 148 of conduit 146, which opens to receptacle 122, may be configured to facilitate placement of an air bladder or other pressurization component 160 (FIGS. 17 through 19) in communication therewith. By way of example, ends 147 and 148 may be threaded to receive complementary threading on hose barbs 149 or other pressure ports of a known type. Hose barbs 149 may be configured for coupling to a tube 150 or an inlet 166 (FIG. 19) of pressurization component 160. Thus, hose barbs 149 facilitate communication between a pressure source (not shown) that communicates either directly or indirectly with tube 150, conduit 146, and pressurization component 160.

Turning reference to FIGS. 17 and 18, an exemplary embodiment of pressurization component 160 that may be used with interface unit 50 (FIGS. 5 and 6), as well as with a variety of other apparatus that are equipped to apply pressure to a body part is depicted.

Pressurization component 160 includes a compliant bladder 162 of a known type, which includes at least two walls 163 and 164 that include peripheries that are secured to one another in an air-tight fashion (e.g., by welds, adhesive, etc.), an interior 165 between walls, and an inlet 166 protruding from one of the walls (eg., wall 163).

Compliant bladder 162 may be somewhat elongate so as to fit within receptacle 92 of monitoring element 90 (FIGS. 10 through 12) or within receptacle 122 of cover 120 (FIGS. 13 through 15). In addition, a compliant bladder 162 so configured may cover and apply pressure to at least a portion of a body part disposed within receptacle 92 or 122. By way of example only, walls 163 and 164 of compliant bladder 162 may be formed from a flexible, pliable material, such as a urethane.

Inlet 166, which may have a tubular appearance, facilitates the introduction of gases (e.g., air) into, and their removal from interior 165 of compliant bladder 162. An enlarged reinforcing base 168 may be disposed around an end 167 of inlet 166. Enlarged reinforcing base 168 may, along with suitable welds or adhesive material, securely fasten inlet 166 to wall 163.

Inlet 166 is configured to be coupled to hose barb 85, which is exposed to receptacle 92, or with a hose barb 149 of cover 120 (FIG. 13). Inlet 166 is formed from a somewhat compliant, somewhat resilient material, such as a urethane. Accordingly, when inlet 166 is coupled to hose barb 85, 149, a substantially air-tight seal may be formed therebetween.

Figure 20:
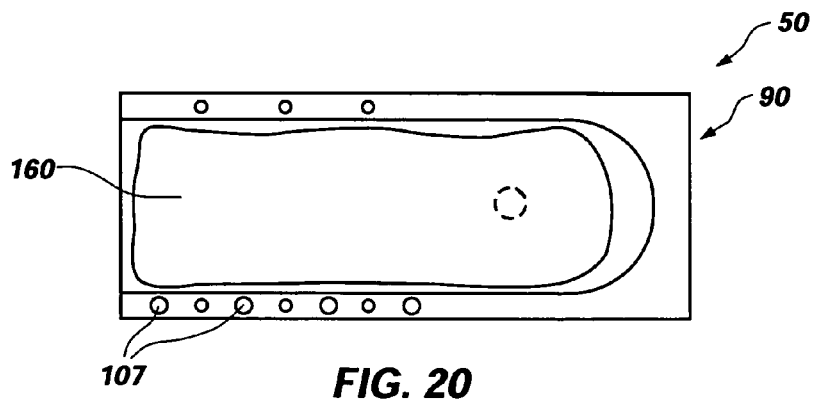
FIG. 20 is a top view of the monitoring element of the interface unit of FIGS. 5 and 6, depicting the assembly of a pressurization component therewith.

As depicted in FIG. 20, two separate pressurization components 160 may be assembled with an interface unit 50 (FIGS. 5 and 6) of the present invention. Alternatively, as shown in FIG. 19, a pair 170 of pressurization components 160a and 160b may include compliant bladders 162a and 162b that are interconnected and that include interiors 165a and 165b that communicate with one another by way of a tube 172 or other conduit disposed therebetween. Like inlet 166, tube 172 may include reinforcing bases 175 and 176 at ends 173 and 174 thereof to enhance the integrity with which tube 172 may be coupled to compliant bladders 162a and 162b, as well as to provide for substantially air-tight communication between tube 172 and interiors 165a and 165b of compliant bladders 162a and 162b.

As pressurization components 160a and 160b of pair 170 communicate with one another through tube 172, it is not necessary for both pressurization components 160a and 160b to include inlets 166. Rather, a single pressurization component 160a, 160b of pair 170 may include an inlet 166, as shown.

With reference to FIGS. 20 through 23, an exemplary method for noninvasively determining the hematocrit of a subject is pictured.

If pressurization of the body part is desired, a pressurization component 160 (FIGS. 17 and 18) may be disposed in receptacle 92 and in receptacle 122 (FIG. 14), as shown in FIG. 20. An inlet 166 of a pressurization component 160 may be coupled to a hose barb 85 (FIG. 10), 149 (FIG. 14) of each receptacle 92, 122. Of course, if an interconnected pair 170 (FIG. 19) of pressurization components 160a and 160b is used, only a single inlet 166 of a pressurization component 160a of pair 170 need be coupled to a hose barb 85, 149.

Figure 21:
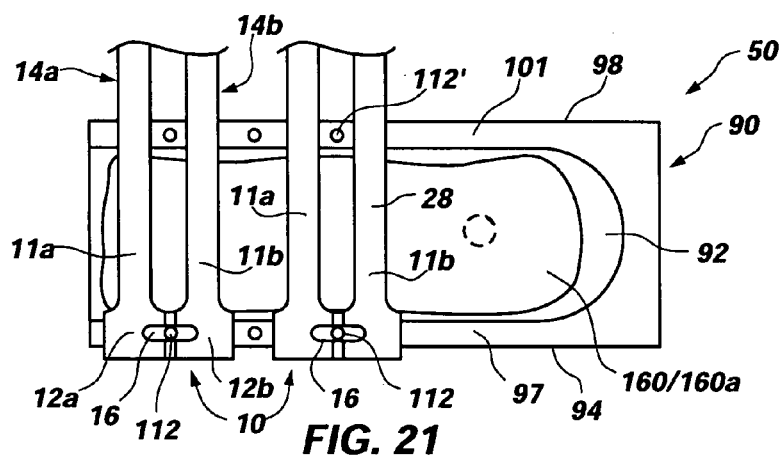
FIG. 21 is a top view of the monitoring element of the interface unit of FIGS. 5 and 6, illustrating the placement of electrode pairs over the receptacle of the monitoring element.

As shown in FIG. 21, two electrode pairs 10 or any other suitable arrangements of electrodes are positioned over receptacle 92, with conductive coating layer 28 being exposed (e.g., facing upwardly) and a portion of each electrical contact element 12a and 12b contacting a corresponding contact 107 (FIG. 20) at upper edge 97 of side 94 of monitoring element 90. Rough alignment of contact elements 12a and 12b and their corresponding contacts 107 may be effected by positioning a guide pin 112 that protrudes from upper edge 97 through apertures 16 of electrode pair 10. Notably, elongate elements 14a and 14b of each electrode pair 10 remain spaced a substantially constant distance apart from one another, despite the positions of electrode pairs 10 relative to guide pins 112.

Electrode pair 10 may include enlarged electrical contact elements 12a, 12b and elongate apertures 16, a combination of features which provides for adjustability of the distance between two electrode pairs 10 positioned across receptacle 92. Accordingly, the positions of electrode pairs 10 or other electrodes that have been disposed across receptacle 92 may be adjusted based on the type of body part to be introduced into receptacle 92, as well as the size of that body part. Such adjustment may be effected either before or after the body part is introduced into receptacle 92.

Additionally, elongate elements 14a and 14b of electrode pair 10 may be positioned on opposite sides of a guide pin 112' that corresponds to the guide pin 112 that extends through apertures 16 of electrode pair 10 and which protrudes from upper edge 101 of side 98 of monitoring element 90.

Of course, if pressurization of a body part to be introduced into receptacle 92 is desired, it is currently preferred that each electrode pair 10 be positioned over receptacle 92 following the positioning of a pressurization component 160, 160a therein.

Figure 22:
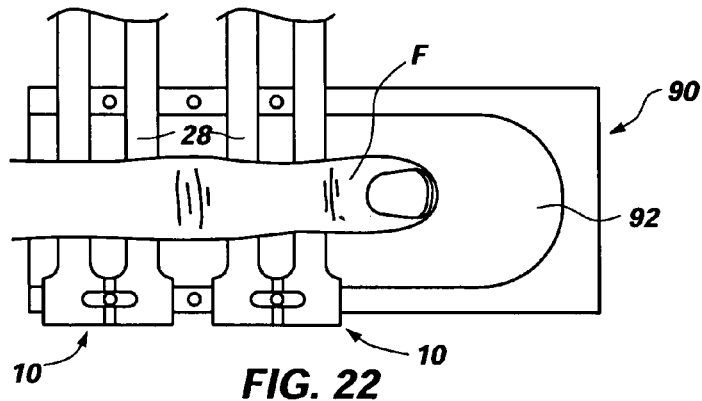
FIG. 22 depicts the placement of a body part, in this case a finger, over the electrode pairs of FIG. 21 and within the receptacle of the monitoring element.

Once electrode pairs 10 have been properly positioned, a body part of a subject, such as the illustrated human finger F, may be introduced into receptacle 92, as shown in FIG. 22. The body part may be introduced into receptacle 92 in such a way that each electrode pair 10 is located between the body part and monitoring element 90 and that a conductive coating layer 28 of each electrode pair 10 contacts the body part.

Figure 23:
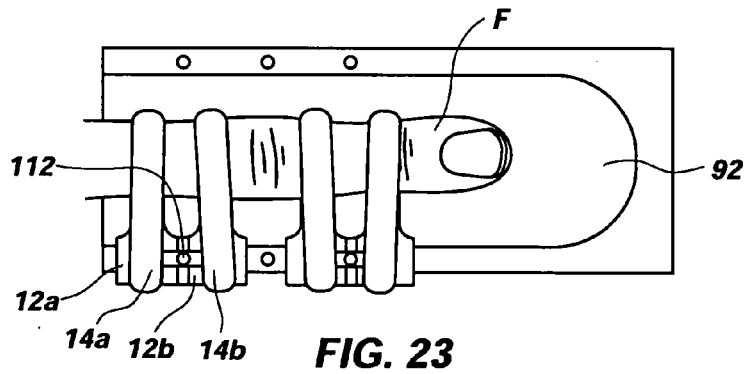
FIG. 23 shows elongate elements of the electrode pairs having been wrapped around the body part.

Thereafter, portions of elongate elements 14a and 14b of each electrode pair 10 that remain exposed may be positioned over the top of the body part (e.g., finger F) within receptacle 92), as shown in FIG. 23. Each elongate element 14a, 14b is positioned over its corresponding contact element 12a, 12b, with guide pins 112 physically separating and, thus, preventing electrical shorting between the electrodes 11a and 11b (FIG. 1) that are carried by adjacent elongate elements 14a and 14b.

Once elongate elements 14a and 14b of electrode pairs 10 (or other electrodes) have been positioned, cover 120 may be placed in a closed position over monitoring element 90, as shown in FIG. 5. Locking element 140 may then be engaged, as described above with reference to FIGS. 13 through 16, to retain cover 120 in the closed position relative to monitoring element 90 and to ensure that an adequate electrical contact is made between each contact 107 of monitoring element 90 and its corresponding, adjacent contact elements 12a, 12b of electrode pairs 10.

Due to the narrow width of monitoring element 90, when the body part that is introduced into receptacle 92 is a finger F, the other fingers of the subject may be comfortably positioned on one or both sides of monitoring element 90. Additionally, base 60 (FIGS. 5 and 6) may be configured to optimize the support that may be provided to the hand (i.e., palm and fingers) of a subject as a noninvasive hematocrit measurement is being obtained.

As can be seen, the configurations of electrode pairs 10 and interface unit 50 simplify the process of applying a number of electrodes to a body part at which a noninvasive hematocrit measurement is to be obtained.

Figure 24:
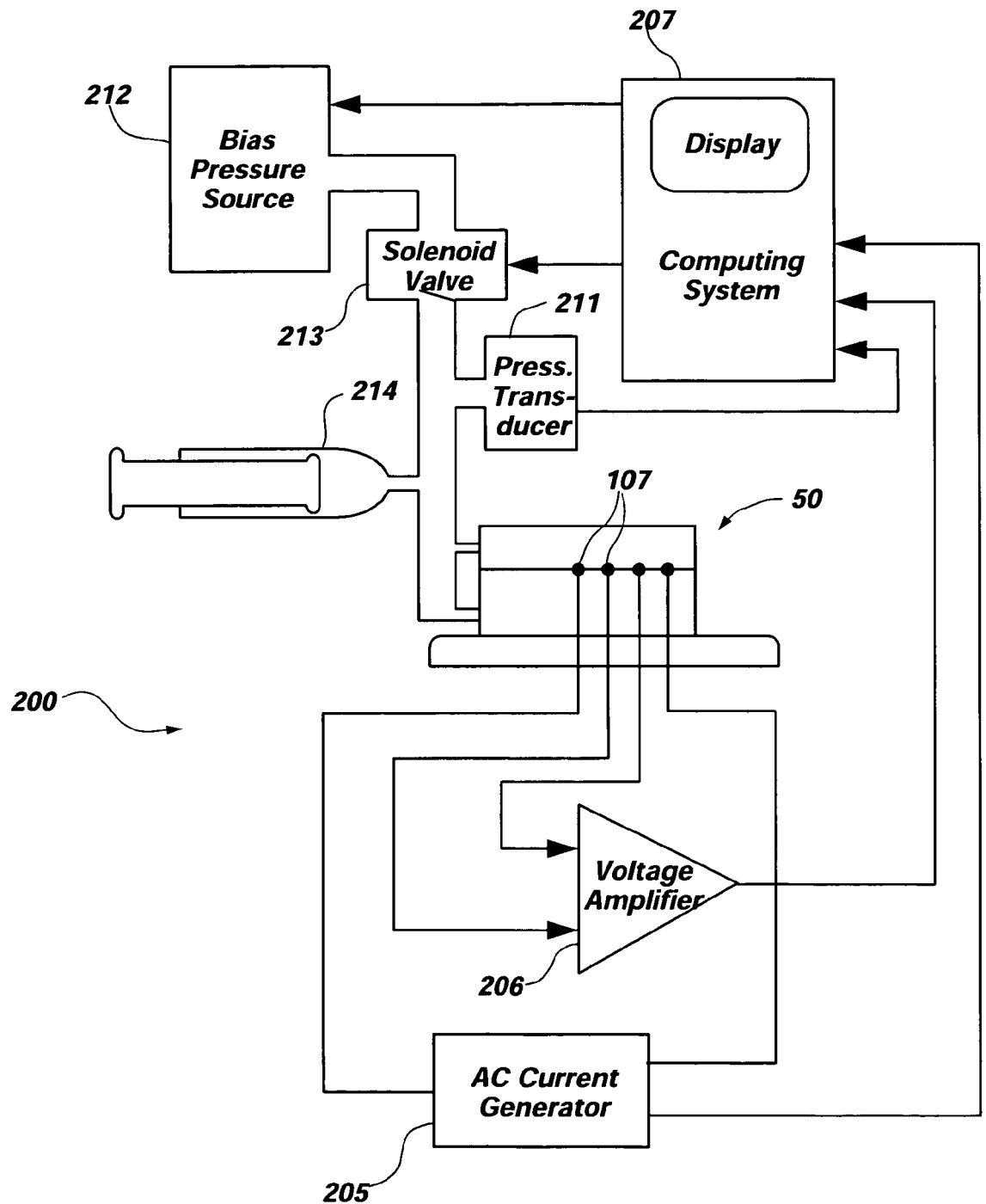
FIG. 24 is a schematic representation of a system that includes the interface unit of FIGS. 5 and 6 and which is useful for noninvasively measuring the hematocrit of a subject.

At this point, the hematocrit of the subject may be noninvasively measured, as described in U.S. Pat. No. 5,526,808, issued to Kaminsky, U.S. Pat. No. 5,642,734, issued to Ruben et al., and U.S. Pat. No. 6,128,518, issued to Billings et al., the entire disclosure of each of these patents hereby being incorporated herein by this reference (hereinafter collectively referred to as "the Microcor Patents"). Such measurement may be effected by use of a system 200 for noninvasively measuring hematocrit, such as that shown in FIG. 24.

In system 200, interface unit 50 communicates with an alternating current generator 205 which, which may be set to deliver a constant current having a waveform combining a low frequency (e.g., about 10 kHz to about 200 kHz) with a high frequency (e.g., about 2 MHz to about 10 MHz) to the outermost contacts 107 shown in FIG. 20 and, thus, to the outermost electrodes 11a and 11b shown in FIG. 21. The inner pair of electrodes 11b and 11a shown in FIG. 21 are connected to the input of a high impedance voltage amplifier 206, which senses the voltage between these electrodes. Both the current generator 205 and the amplifier 206 are connected to a processing element 207 (e.g., a processor, computer or other group of processors, etc., which may be part of or associated with a computing system).

A pressure transducer 211 may communicate pneumatically with pressurization components 160 (FIG. 20) to sense the bias pressure and the pulse pressure from which blood volume on each pulse is computed. Pressure transducer 211 may also communicate electrically with processing element 207 to transmit signals representative of the measured pressures thereto.

A pressure source 212 may also communicate pneumatically with pressurization component 160 (FIG. 20). Operation of pressure source 212 may be under control of processing element 207. Alternatively, or in addition, a valve 213 (e.g., a solenoid valve), which may be under control of processing element 207, may be included in system 200 to control communication between pressure source 212 and pressurization component 160. By controlling valve 213, the amount of positive pressure that is applied to a body part (e.g., finger F) disposed within receptacles 92 and 122 (FIGS. 5 and 23) may also be controlled. Pressure source 212 may be of any configuration having the ability to supply air at a pressure as high as approximately 200 mmHg above the ambient atmospheric pressure.

A calibration device 214 may also communicate pneumatically with pressurization component 160 (FIG. 20). Calibration device 214 is configured to cause pressurization component 160 to apply a precisely known amount of positive pressure to a portion of a body part located within receptacles 92 and 122 (FIGS. 5 and 23) to facilitate calibration of a pressure change that corresponds to a given volume. Calibration device 214 may be as simple as a small calibrated medical syringe, as depicted, which can be manually operated, or it may be a more complex device, controlled by the processing element 207 and capable of producing precise volume pulses of close to the same magnitude as the cardiac pulses for dynamic calibration.

Once the subject's hematocrit has been measured, the body part (e.g., finger F) may be removed from interface unit 50. For example, the process that has been described above in reference to FIGS. 5, 22, and 23 may be reversed. Thereafter, electrode pairs 10 (FIG. 21) and/or pressurization components 160 may be removed from interface unit 50, making way for replacement electrode pairs 10 or pressurization components 160, which may be used to noninvasively measure the hematocrit of another subject.

Signals from current generator 205, amplifier 206, and pressure transducer 211 may be communicated to processing element 207, which evaluates and processes the signals in the manner described in the Microcor Patents to noninvasively determine the hematocrit of the subject.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed is:

1. An electrode for use in obtaining a noninvasive impedance measurement of tissue constituents from a subject, comprising:
   an electrically insulative substrate; and
   at least two discrete, linear, elongate conductive elements carried by the electrically insulative substrate with at least regions of adjacent conductive elements that are not carried by the electrically insulative substrate being spaced apart from one another a distance that facilitates the noninvasive impedance measurement of tissue constituents, each elongate conductive element including a contact region.

2. The electrode of claim 1, wherein a pair of elongate conductive elements of the at least two elongate conductive elements extends in substantially a common direction.

3. The electrode of claim 2, wherein the elongate conductive elements of the pair are oriented substantially parallel to one another.

4. The electrode of claim 3, wherein the elongate conductive elements of the pair have substantially the same widths.

5. The electrode of claim 4, wherein the elongate conductive elements of the pair are spaced apart from one another by a distance which is substantially the same as the width of each elongate element.

6. The electrode of claim 5, wherein the electrically insulative substrate has a width equal to about four times the width of each elongate element.

7. The electrode of claim 6, wherein a gap between the elongate elements of the pair is positioned substantially centrally relative to the width of the electrically insulative substrate.

8. The electrode of claim 1, wherein the contact region includes at least one aperture formed therethrough.

9. The electrode of claim 8, wherein the at least one aperture is elongate.

10. The electrode of claim 1, wherein each elongate conductive element includes an electrical contact configured to be folded in half to include oppositely facing electrically conductive surfaces.

11. A strip of electrodes, comprising two offset rows of at least partially overlapping electrode pairs, each electrode pair including:
a common contact region; and
a pair of spaced apart elongate elements extending from the common contact region and oriented substantially parallel to one another,
common contact regions of adjacent electrode pairs in the same row being positioned adjacent to one another and forming an edge of the strip,
elongate elements of electrode pairs in the same row being aligned with one another and oriented substantially parallel to each other,
adjacent elongate elements of each row being spaced apart by an elongate element of an electrode pair of the other row.

12. The strip of claim 11, wherein all of the elongate elements of the electrode pairs have substantially the same widths and are spaced apart from one another by a distance which is substantially equal to a width of each elongate element.

13. The strip of claim 11, comprising:
a substantially confluent dielectric layer;
a patterned conductive layer on the substantially confluent dielectric layer; and
a conductive coating layer over the patterned conductive layer only at locations of the strip that include the elongate elements.

14. The strip of claim 13, wherein the patterned conductive layer forms a pair of electrical contacts at the common contact region of each electrode pair and an electrode that communicates with a corresponding electrical contact and forms a part of each elongate element.

15. The strip of claim 13, wherein the substantially confluent dielectric layer includes at least one row of apertures formed through the common contact regions of each row of electrode pairs.

16. The strip of claim 15, wherein the substantially confluent dielectric layer includes two rows of apertures formed through the common contact regions of each row of electrode pairs.

17. The strip of claim 16, wherein the common contact region of each electrode pair is configured to be folded in half such that two apertures formed therethrough are aligned with one another and a pair of electrical contacts thereon are exposed to both major surfaces of the electrode pair.

18. An electrode strip, comprising:
a pair of electrodes spaced apart from one another by a distance that facilitates a noninvasive impedance measurement of tissue constituents; and
at least another electrode interleaved between electrodes of the pair and configured to be removed from between the pair of electrodes prior to use of the electrodes and the at least another electrode.

19. The electrode strip of claim 18, wherein the pair of electrodes are physically secured to one other by way of an electrically non-conductive element.

20. The electrode pair of claim 18, wherein the pair of electrodes extend substantially parallel to one another.

21. The electrode pair of claim 18, wherein a contact region of each electrode is configured to be folded in half such that a pair of electrical contacts are exposed to both major surfaces of the electrode.

* * * * *